US010407372B2

(12) United States Patent
Simpson et al.

(10) Patent No.: US 10,407,372 B2
(45) Date of Patent: Sep. 10, 2019

(54) HYDROFORMYLATION PROCESS

(71) Applicant: Dow Technology Investments LLC, Midland, MI (US)

(72) Inventors: Kathleen Simpson, Gandeeville, WV (US); Gerald L. Smith, Dickinson, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 16/081,682

(22) PCT Filed: Mar. 15, 2017

(86) PCT No.: PCT/US2017/022474
§ 371 (c)(1),
(2) Date: Aug. 31, 2018

(87) PCT Pub. No.: WO2017/160956
PCT Pub. Date: Sep. 21, 2017

(65) Prior Publication Data
US 2019/0023637 A1    Jan. 24, 2019

Related U.S. Application Data (60) Provisional application No. 62/310,181, filed on Mar. 18, 2016.

(51) Int. Cl.
| | |
|---|---|
| C07C 45/50 | (2006.01) |
| C07C 45/82 | (2006.01) |
| C07C 45/72 | (2006.01) |
| C07C 45/78 | (2006.01) |
| B01D 3/16 | (2006.01) |
| B01D 3/32 | (2006.01) |
| B01D 5/00 | (2006.01) |
| C07C 47/02 | (2006.01) |

(52) U.S. Cl.
CPC ............... *C07C 45/82* (2013.01); *B01D 3/16* (2013.01); *B01D 3/32* (2013.01); *B01D 5/006* (2013.01); *B01D 5/009* (2013.01); *C07C 45/50* (2013.01); *C07C 45/72* (2013.01); *C07C 45/783* (2013.01); *C07C 45/786* (2013.01); *C07C 47/02* (2013.01)

(58) Field of Classification Search
CPC ....... C07C 45/50; C07C 45/82; C07C 45/783; B01D 3/16
See application file for complete search history.

(56) References Cited

U.S. PATENT DOCUMENTS

| | | | |
|---|---|---|---|
| 3,527,809 A | 9/1970 | Pruett et al. | |
| 4,148,830 A | 4/1979 | Pruett et al. | |
| 4,166,773 A | 9/1979 | Higley et al. | |
| 4,210,426 A | 7/1980 | Sridhar | |
| 4,247,486 A | 1/1981 | Brewester et al. | |
| 4,248,802 A | 2/1981 | Kuntz | |
| 4,277,627 A | 7/1981 | Bryant et al. | |
| 4,287,369 A * | 9/1981 | Harris | C07C 45/50 568/454 |
| 4,447,661 A | 5/1984 | Hoshiyama et al. | |
| 4,479,012 A | 10/1984 | Fischer et al. | |
| 4,593,127 A | 6/1986 | Bunning et al. | |
| 4,668,651 A | 5/1987 | Billig et al. | |
| 4,731,486 A | 3/1988 | Abatjoglou et al. | |
| 4,769,498 A | 9/1988 | Billig et al. | |
| 4,774,361 A | 9/1988 | Maher et al. | |
| 5,001,274 A | 3/1991 | Bunning | |
| 5,087,763 A | 2/1992 | Sorensen | |
| 5,105,018 A | 4/1992 | Miyazawa et al. | |
| 5,110,990 A | 5/1992 | Blessing et al. | |
| 5,268,514 A | 12/1993 | Bahrmann et al. | |
| 5,288,918 A * | 2/1994 | Maher | B01J 31/185 558/71 |
| 5,312,996 A | 5/1994 | Packett | |
| 5,367,106 A | 11/1994 | Unruh et al. | |
| 5,430,194 A | 7/1995 | Barner et al. | |
| 5,462,986 A | 10/1995 | Bahrmann et al. | |
| 5,463,137 A | 10/1995 | Ramachandran et al. | |
| 5,516,965 A | 5/1996 | Hershkowitz et al. | |
| 5,675,041 A | 10/1997 | Kiss et al. | |
| 5,681,473 A | 10/1997 | Miller et al. | |
| 5,728,893 A * | 3/1998 | Becker | B01J 19/18 568/451 |
| 5,929,289 A | 7/1999 | Abatjoglou et al. | |
| 5,952,530 A | 9/1999 | Argyropoulos et al. | |
| 6,482,992 B2 | 11/2002 | Scholz et al. | |
| 6,969,777 B2 | 11/2005 | Walz et al. | |

(Continued)

FOREIGN PATENT DOCUMENTS

| | | |
|---|---|---|
| CN | 102826969 A | 12/2012 |
| CN | 102826973 A | 12/2012 |

(Continued)

OTHER PUBLICATIONS

OXO Alcohols, Process Economics Program Report 21D, Dec. 1999, Abstract, pp. 1 to xi, 4-24 to 4-36, and E-5.
PCT/US2017/022474, International Search Report dated Sep. 21, 2017.
PCT/US2017/022474, International Preliminary Report on Patentability dated Sep. 18, 2018.
PCT/US2017/022474, Written Opinion of the International Searching Authority dated Sep. 21, 2017.

(Continued)

*Primary Examiner* — Sikarl A Witherspoon (57) ABSTRACT

Embodiments of the present invention relate to processes for the hydroformylation of olefins to produce aldehydes. In some embodiments, processes of the present invention are capable of maintaining high $C_2$-$C_4$ olefin conversion and/or provide more compact hydroformlyation processes.

16 Claims, 1 Drawing Sheet

(56) References Cited

U.S. PATENT DOCUMENTS

| | | | |
|---|---|---|---|
| 7,405,329 B2 | 7/2008 | Beadle et al. | |
| 8,404,903 B2 * | 3/2013 | Cox | C07C 45/50 |
| | | | 568/451 |
| 9,695,098 B2 * | 7/2017 | Miller | C07C 45/50 |
| 2003/0176743 A1 | 9/2003 | Walz et al. | |
| 2010/0048959 A1 | 2/2010 | Sigl et al. | |
| 2011/0282108 A1 * | 11/2011 | Ko | C07C 29/141 |
| | | | 568/883 |

FOREIGN PATENT DOCUMENTS

| | | | |
|---|---|---|---|
| CN | 103130623 A | 6/2013 | |
| CN | 101293818 A | 10/2018 | |
| DE | 323557 C | 7/1920 | |
| EP | 0016285 A2 | 10/1980 | |
| EP | 652451 A1 | 5/1995 | |
| EP | 2390242 A2 | 11/2011 | |
| GB | 1387657 A | 3/1975 | |
| WO | 95/08525 A1 | 3/1995 | |
| WO | 2012/008717 A2 | 1/2012 | |
| WO | 2014/178912 A1 | 11/2014 | |
| WO | 2015/094781 A1 | 6/2015 | |
| WO | 2015/094813 A1 | 6/2015 | |

* cited by examiner

HYDROFORMYLATION PROCESS

FIELD

The present invention relates to processes for the hydroformylation of olefins to produce aldehydes.

BACKGROUND

A number of hydroformylation processes involve the further processing of vent streams from hydroformylation reactors. The vent streams are present to prevent the build up of inert impurities, such as $N_2$, $CO_2$, Ar, $CH_4$ and hydrocarbons, by purging them from the process. The inerts may get into the process as impurities in the feeds. These are generally vented prior to the product-catalyst separation zone to reduce the load on these separation systems. A significant amount of these inerts are also dissolved in the crude aldehyde product which must be removed as vents or purges in downstream refining. Unfortunately, the process of venting these inerts also tends to result in the loss of valuable reactants, such as olefin.

A number of prior processes have sought to recover and recycle the olefin contained in these vents. However, such processes typically involved complex, expensive designs and many were limited to higher boiling olefins. For example, U.S. Pat. No. 4,287,369 discloses separating unreacted olefin from aldehyde via distillation and recycling (optionally with redistilling) the olefin back to the reaction zone. This approach relies on being able to condense the olefin at the top of the distillation tower to deliver the olefin as a liquid back to the hydroformylation system (or olefin/paraffin distillation system). To achieve this at the pressures contemplated by the '369 patent, the crude aldehyde must be distilled at over 190° C. which will result in high heavies formation. Table 1 of the '369 patent shows that a ΔT of over 100° C. between lines 44 (olefin/paraffin) and 46 (aldehyde) is needed in the distillation column to separate the olefin/paraffin mixture from the aldehyde.

There remains a need for improved hydroformylation processes that are more compact with lower capital requirements. There also remains a need for improved hydroformylation processes that are capable of maintaining high $C_2$-$C_4$ olefin conversion but at lower capital cost.

SUMMARY

The present invention provides hydroformylation processes that are capable of maintaining high $C_2$-$C_4$ olefin conversion at a lower capital cost. In some embodiments, processes of the present invention provide more compact hydroformlyation process with lower capital costs. Surprisingly, hydroformylation processes of the present invention provide such advantages without hydrocarbon accumulation.

In one aspect, a process of the present invention comprises (a) contacting CO, $H_2$, and at least one $C_2$-$C_4$ olefin in a reaction zone in the presence of a hydroformylation catalyst to form at least one aldehyde product; (b) removing an aldehyde-containing liquid from the reaction zone and sending it to a product-catalyst separation zone; (c) transporting a first stream from the product-catalyst separation zone to the reaction zone, wherein the first stream is a liquid comprising at least a portion of the hydroformylation catalyst, at least a portion of the aldehyde product, and unreacted olefin; (d) removing a second stream from the product-catalyst separation zone, wherein the second stream comprises at least a portion of the aldehyde product, unreacted olefin, and one or more paraffins; (f) transferring the second stream to a syngas stripper wherein a gas comprising CO and $H_2$ separates the unreacted olefin from the aldehyde; (g) providing the gas leaving the syngas stripper to a condenser to provide a second liquid comprising a majority of the aldehyde, at least a portion of the unreacted olefin from the syngas stripper, and at least a portion of the paraffins from the syngas stripper, and to provide a gas stream comprising CO, $H_2$, the remainder of the unreacted olefin from the syngas stripper, and the remainder of the paraffins from the syngas stripper; (h) providing the gas stream leaving the condenser in (g) to the reaction zone; (i) transferring the second liquid from the condenser in (g) to a first distillation system wherein at least a portion of the unreacted olefin and paraffins are distilled from the aldehyde; (j) transferring the gas from the first distillation system to a second distillation system wherein the unreacted olefin and paraffins are separated into an olefin-enriched stream and a paraffin-enriched stream, wherein the gas is transferred from the first distillation system to the second distillation system without a compressor; and (k) transferring the olefin-enriched stream to the reaction zone.

In another aspect, a process of the present invention comprises (a) contacting CO, $H_2$, and at least one $C_2$-$C_4$ olefin in a reaction zone in the presence of a hydroformylation catalyst to form at least one aldehyde product; (b) removing an aldehyde-containing liquid from the reaction zone and sending it to a product-catalyst separation zone, wherein the product-catalyst separation zone comprises a liquid withdrawal port and a vapor withdrawal port; (c) transporting a liquid comprising at least a portion of the hydroformylation catalyst, at least a portion of the aldehyde product, and unreacted olefin from the liquid withdrawal port to the reaction zone; (d) removing a vapor from the vapor withdrawal port, wherein the vapor comprises at least a portion of the aldehyde product, unreacted olefin, and one or more paraffins; (e) condensing the vapor to generate a second liquid; (f) transferring the second liquid to a syngas stripper wherein a gas comprising CO and $H_2$ separates the unreacted olefin from the aldehyde; (g) providing the gas leaving the syngas stripper to a condenser to provide a second liquid comprising a majority of the aldehyde, at least a portion of the unreacted olefin from the syngas stripper, and at least a portion of the paraffins from the syngas stripper, and to provide a gas stream comprising CO, $H_2$, the remainder of the unreacted olefin from the syngas stripper, and the remainder of the paraffins from the syngas stripper; (h) providing the gas stream leaving the condenser in (g) to the reaction zone; (i) transferring the second liquid from the condenser in (g) to a first distillation system wherein at least a portion of the unreacted olefin and paraffins are distilled from the aldehyde; (j) transferring the gas from the first distillation system to a second distillation system wherein the unreacted olefin and paraffins are separated into an olefin-enriched stream and a paraffin-enriched stream, wherein the gas is transferred from the first distillation system to the second distillation system without a compressor; and (k) transferring the olefin-enriched stream to the reaction zone.

These and other embodiments are described in more detail in the Detailed Description.

DETAILED DESCRIPTION

The disclosed process comprises contacting CO, $H_2$, and at least one $C_2$-$C_4$ olefin under hydroformylation conditions sufficient to form at least one aldehyde product in the presence of a catalyst comprising, as components, a transition metal and an organophosphorous ligand. Optional process components include an amine and/or water.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reactor, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

Hydrogen and carbon monoxide are required for the process. These may be obtained from any suitable source, including petroleum cracking and refinery operations. Synthesis gas or "syngas" is the name given to a gas mixture that contains varying amounts of CO and $H_2$. Production methods are well known and include, for example: (1) steam reforming and partial oxidation of natural gas or liquid hydrocarbons; and (2) the gasification of coal and/or biomass. Hydrogen and CO typically are the main components of syngas, but syngas may contain carbon dioxide and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The substituted or unsubstituted olefinic unsaturated starting material reactants that may be employed in the hydroformylation process according to embodiments of the present invention include olefinic unsaturated compounds containing from 2 to 4, preferably 3 carbon atoms. In addition, commercially available alpha olefins containing 2 to 4 carbon atoms may contain minor amounts of corresponding internal olefins and/or their corresponding saturated hydrocarbon, as well as minor amount of olefins containing five or more carbon atoms, such that commercially available olefins need not necessarily be purified from same prior to being hydroformylated. Illustrative mixtures of olefinic starting materials that can be employed in the hydroformylation reactions include, for example, mixed butenes, e.g., Raffinate I and II. Further, such olefinic unsaturated compounds and the corresponding aldehyde products derived therefrom may also contain one or more groups or substituents which do not unduly adversely affect the hydroformylation process or the process of this invention such as described, for example, in U.S. Pat. Nos. 3,527,809, 4,769,498 and the like.

Illustrative alpha and internal olefins that can be used in embodiments of the present invention include, for example, ethylene, propylene, 1-butene, 2-butene (cis/trans), and 2-methyl propene (isobutylene).

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,380 and 4,247,486. Indeed, while one may employ, if desired, any suitable solvent at the start-up of a continuous process, the primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

Illustrative metal-organophosphorous ligand complexes employable in such hydroformylation reactions encompassed by this invention include the metal-organophosphorous ligand complex catalysts as well as methods for their preparation are well known in the art and include those disclosed in the above mentioned patents. In general, such catalysts may be preformed or formed in situ as described in such references and consist essentially of metal in complex combination with an organophosphorous ligand. It is believed that carbon monoxide is also present and complexed with the metal in the active species. The active species may also contain hydrogen directly bonded to the metal.

The catalyst useful in the hydroformylation process includes a metal-organophosphorous ligand complex catalyst which can be optically active or non-optically active. The permissible metals that make up the metal-organophosphorous ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of metals from Groups 8, 9 and 10 may also be employed. In general, any metal-organophosphorous ligand known to be useful as a catalyst in a hydroformylation process can be used in embodiments of the present invention.

The process of the invention employs one or more primary hydroformylation reactors followed by a product-catalyst separation zone. The separation zone produces a crude product stream and a catalyst recycle stream. The crude product stream comprises the desired aldehyde product as well as unreacted raw materials, such as olefin and syngas. An unrefined product stream is separated from the unreacted raw materials following the product-catalyst separation zone using techniques well known to those skilled in the art. The unreacted raw materials may then be supplied to a separate, secondary reactor, and the liquid output from the secondary reactor is fed to the same product-catalyst separation zone as described in WO2015/094813A1. The catalyst recycle stream from the product-catalyst separation zone is split, with a portion being recycled to at least one of the primary reactors and a portion being recycled to the secondary reactor (if present).

The hydroformylation process may be carried out using one or more suitable reactor types such as, for example, a tubular reactor, venturi reactor, a bubble column reactor, or a continuous stirred tank reactor. A reaction zone may be fitted with one or more internal and/or external heat exchanger(s) in order to control temperature fluctuations, and to prevent any possible "runaway" reaction temperatures.

Each reactor vessel may comprise a single reaction zone or multiple reaction zones, such as, for example, described in U.S. Pat. No. 5,728,893. In one embodiment of the invention, two reaction zones are present in a single reactor vessel. The term "first reaction zone" refers to the first reaction zone in the primary reactor. Multistaged reactors can be designed with internal, physical barriers that create more than one reaction zone or theoretical reactive stage per vessel. In effect, a number of reactor zones are contained inside a single continuous stirred tank reactor vessel. Putting multiple reaction zones in a single vessel is a cost effective way of using reactor vessel volume, and significantly reduces the number of vessels that otherwise would be required to achieve the same results. Fewer vessels reduces the overall capital required and maintenance concerns associated with having separate vessels and agitators. Within a reactor, reaction zones can be arranged in series or in parallel.

The choice of suitable materials of construction for process equipment can be readily made by those skilled in the art. The materials employed should be substantially inert to the starting materials and the reaction mixture, and the process equipment should be able to withstand the reaction temperatures and pressures. For example, the hydroformylation processes may be conducted in either glass lined, stainless steel or similar type reaction equipment.

Means to introduce and/or adjust the quantity of starting materials or ingredients introduced batch wise, semi-continuously or continuously into the reaction zone during the course of the reaction can be conveniently utilized in the process, and such means are useful to maintain the desired molar ratio of the starting materials. The reaction steps may be effected by the incremental addition of one of the starting materials to the other.

The process may be conducted in any batch, continuous or semi-continuous fashion and may involve any catalyst liquid and/or gas recycle operation desired. It is generally preferred to carry out the hydroformylation process in a continuous manner Continuous hydroformylation processes are well known in the art. The catalyst, the reaction conditions, and the equipment in the hydroformylation reaction zone are not particularly critical for this invention.

After the reaction, the product is separated from the catalyst and the catalyst is recycled. Any suitable technique for separating the product from the reactor effluents can be employed. Unit operations suitable for use in the product-catalyst separation zone are well known to those skilled in the art and can comprise, for example, solvent extraction, membrane separation, crystallization, phase separation or decanting, filtration, distillation, and the like, or any combination thereof. Examples of distillation include flashing, wiped film evaporation, falling film evaporation, gas stripping, and distillation in any other type of conventional distillation equipment. Examples of membrane separation processes are disclosed in U.S. Pat. Nos. 5,430,194 and 5,681,473. For the purposes of the invention, the term "vaporization" will be used to encompass these unit operations, and the term "vaporizer" is used synonymously with "product-catalyst separation zone."

The preferred and conventional method of product-catalyst separation is distillation, preferably in a falling-film evaporator, in one or more stages under normal, reduced or elevated pressure, as appropriate, with the non-volatilized metal catalyst-containing residue being recycled to the reactors. For example, separation and catalyst recycle for a single train is described in U.S. Pat. No. 5,288,918, and the separation technique employed there can be employed in the process of the invention. Preferably, the liquid effluent of the primary reactor train is fed to a vaporizer and the liquid effluent of any secondary reactor train is fed to the same vaporizer as described in WO2015/094781A1. The non-vaporized, liquid effluent from the common vaporizer advantageously is split and recycled to the primary and secondary reactor trains.

The common vaporizer may comprise multiple vaporization units in series, such as high pressure and low pressure vaporizers, as shown, for example, in CN 102826969. For example, the primary reactor and any secondary reactor each may have its own high pressure vaporizer, and each non-volatilized stream from the high pressure vaporizers is fed to the common low pressure vaporizer. This allows recycling of pressurized lights, such as ethylene, propylene or butene, to each reactor from its own high pressure vaporizer, and the final product-catalyst separation is performed in the common low pressure vaporizer. In any case, the common final catalyst recycle stream is split, either at or after the final vaporizer, and is sent back to the reactors.

As indicated above, the desired aldehydes are recovered from the reaction mixture. For example, the recovery techniques disclosed in U.S. Pat. Nos. 4,166,773, 4,148,830, 4,247,486, and 8,404,903 can be employed. In a continuous liquid catalyst recycle process, the portion of the liquid reaction mixture (containing aldehyde product, catalyst, etc.), i.e., reaction fluid, removed from the reactors can be passed to a product-catalyst separation zone, e.g., vaporizer/separator, wherein the desired aldehyde product can be separated via distillation, in one or more stages, under normal, reduced or elevated pressure, from the liquid reaction fluid, then condensed and collected in a product receiver, and further refined or purified if desired. The remaining non-volatilized catalyst containing liquid reaction mixture is recycled back to the reactors, as may any other volatile materials, e.g., unreacted olefin, together with any hydrogen and carbon monoxide after separation thereof from the condensed aldehyde product. In general, it is preferred to separate the desired aldehydes from the catalyst-containing reaction mixture under reduced pressure and at low temperatures so as to avoid possible degradation of the organophosphorous ligand and reaction products.

More particularly, distillation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is generally preferred that such aldehyde distillation take place under a total gas pressure that is lower than the total gas pressure employed during hydroformylation when low boiling aldehydes (e.g., $C_3$ to $C_6$) are involved. In general, distillation pressures ranging from vacuum pressures up to a total gas pressure of 340 kPa (49.3 psia) are sufficient for most purposes.

Various types of recycle procedures are known in the art and may involve the liquid recycling of the metal-organophosphorous complex catalyst fluid separated from the desired aldehyde reaction product(s), such as disclosed, for example, in U.S. Pat. No. 4,148,830. A continuous liquid catalyst recycle process is preferred. Examples of suitable liquid catalyst recycle procedures are disclosed in U.S. Pat. Nos. 4,248,802; 4,668,651; 4,731,486; 4,774,361; 5,110,990; and 5,952,530.

For example, the catalyst recycle procedure generally involves withdrawing a portion of the liquid reaction medium containing the catalyst and aldehyde product from at least one of the hydroformylation reactors, either continuously or intermittently, and recovering the aldehyde product therefrom by use of a product-catalyst separation zone. Collection of the removed aldehyde product, typically by condensation of the volatilized materials, and separation and further refining thereof, e.g., by distillation, can be carried out in any conventional manner, and the crude aldehyde product can be passed on for further purification and isomer separation, if desired, and any recovered reactants, e.g., olefinic starting material and syngas, can be recycled in any desired manner to the hydroformylation zone (reactor). The aldehyde products can be refined by distillation, including multi-step distillation, to remove unreacted material and recover a purified product. The recovered metal catalyst-containing raffinate of such separation or recovered non-volatilized metal catalyst-containing residue of such separation can be recycled, to one or more of the hydroformylation reactors as described above.

The initially isolated crude aldehyde stream from the product-catalyst separation zone described above contains substantial amounts of unreacted olefin as well as other side products including paraffins (alkanes). The paraffins may have originated in the olefin feed or have resulted from hydrogenation of the olefin in the hydroformylation zone. The separation of the paraffins from the olefin during any recovery and recycle process is critical to avoid excessive buildup of the unreactive paraffins which can eventually "choke" the system. Embodiments of the present invention advantageously separate and recover these unreacted olefins.

However, there are difficulties in separating the olefin/paraffin mixture from the aldehyde due to two conflicting constraints. The first constraint is the thermal sensitivity of the aldehyde; due to the thermal sensitivity of aldehydes, low temperatures are preferred to avoid aldehyde condensation reactions. Unfortunately, the $C_2$-$C_4$ olefins are gasses at ambient temperature and pressure such that expensive cryogenic condensers or compressors would be required (to recycle back to the reaction system), which are economically unfavorable. Alternatively, the distillation could be done at elevated pressure rendering the olefins liquid at cooling water temperatures, but this would require elevated distillation temperatures in conflict with the first constraint.

The second related constraint is the olefin/paraffin separation. Again, these $C_2$-$C_4$ compounds are gases at ambient pressure thus requiring elevated pressures to do the distillation without cryogenic cooling. Normally, this would also require a compressor to get the gases to elevated pressure (assuming the vaporizer was initially running at reduced pressure to avoid aldehyde condensation). Compressors are often undesirable because they are expensive, energy intensive, and high maintenance items.

The present invention advantageously resolves these conflicting constraints without the use of cryogenic cooling or compressors by dissolving the gases in a liquid and generating the needed pressures using liquid pumps. In simple terms, the condensed crude aldehyde with the dissolved olefin/paraffin mixture is pumped as a liquid to a syngas stripper wherein the majority of the olefin/paraffin mixture is removed as a gas at elevated pressure. In a syngas stripper, bubbles of syngas flow up through the liquid medium, dissolve, and remove the volatile gases (primarily olefins and paraffins) from the higher boiling aldehydes without needing elevated temperatures. The resulting liquid effluent aldehyde product which is substantially free of unreacted olefin is sent on for further processing. The gas effluent is sent to a condenser where some vaporized aldehyde and nearly all the olefin/paraffin mixture are collected and delivered at pressure to a distillation column to separate the aldehyde from the olefin/paraffin mixture. The syngas stripper greatly concentrates the olefin/paraffin level in the stream making the distillation much easier. The aldehyde in the bottom stream is recycled back to the system. The olefin/paraffin mixture is then sent to a second column at the pressure needed to conduct the olefin/paraffin separation without the need for a compressor or cryogenic cooling. Syngas used in the stripper is sent on to the hydroformylation reaction system and thus is not wasted. Any uncondensed aldehyde present in this syngas stream is also recovered.

In contrast to the prior art, the distillation column separating the aldehyde from the olefin/paraffin need not run as harshly since any olefin left in the bottom stream will be recycled back to the hydroformylation reactor. Typically the feed to this distillation column comprises 20% or more olefin/paraffin, but the tails may have roughly ½ as much due to the recycle nature of this process. This results in fewer heavies formation as compared to the prior art.

After removal of the unreacted olefin, the resulting aldehyde product stream can be processed by conventional means. For example, the aldehyde products can be separated and separately processed by hydrogenation or aldolisation/hydrogenation to alcohols. Alternatively, the aldehyde products are not separated but are processed together. For example, the aldehyde mixture can be hydrogenated and the individual alcohols can be separated after hydrogenation. Another possibility involves aldolization/hydrogenation to a mixture of alcohols and higher alcohols followed by distillation to isolate the individual alcohols. An example of such multiple processing schemes is given in WO 2012/008717 A2.

A process of the present invention, according to one embodiment, comprises (a) contacting CO, $H_2$, and at least one $C_2$-$C_4$ olefin in a reaction zone in the presence of a hydroformylation catalyst to form at least one aldehyde product; (b) removing an aldehyde-containing liquid from the reaction zone and sending it to a product-catalyst separation zone; (c) transporting a first stream from the product-catalyst separation zone to the reaction zone, wherein the first stream is a liquid comprising at least a portion of the hydroformylation catalyst, at least a portion of the aldehyde product, and unreacted olefin; (d) removing a second stream from the product-catalyst separation zone, wherein the second stream comprises at least a portion of the aldehyde product, unreacted olefin, and one or more paraffins; (f) transferring the second stream to a syngas stripper wherein a gas comprising CO and $H_2$ separates the unreacted olefin from the aldehyde; (g) providing the gas leaving the syngas stripper to a condenser to provide a second liquid comprising a majority of the aldehyde, at least a portion of the unreacted olefin from the syngas stripper, and at least a portion of the paraffins from the syngas stripper, and to provide a gas stream comprising CO, $H_2$, the remainder of the unreacted olefin from the syngas stripper, and the remainder of the paraffins from the syngas stripper; (h) providing the gas stream leaving the condenser in (g) to the reaction zone; (i) transferring the second liquid from the condenser in (g) to a first distillation system wherein at least a portion of the unreacted olefin and paraffins are distilled from the aldehyde; (j) transferring the gas from the first distillation system to a second distillation system wherein the unreacted olefin and paraffins are separated into an olefin-enriched stream and a paraffin-enriched stream, wherein the gas is transferred from the first distillation system to the second distillation system without a compressor; and (k) transferring the olefin-enriched stream to the reaction zone.

In some embodiments, the second stream from the product-catalyst separation zone is a liquid. In some such embodiments, the product-catalyst separation zone can comprise a membrane separation process.

In some embodiments, the second stream from the product-catalyst separation zone is a vapor. In some embodiments where the second stream from the product-catalyst separation zone comprises a vapor, the product-catalyst separation zone can comprise a vaporizer. In some embodiments where the second stream from the product-catalyst separation zone comprises a vapor, the product-catalyst separation zone can comprise a vaporizing zone and a vapor/liquid separation zone, the aldehyde-containing liquid from the reaction zone is heated in the vaporizing zone to generate the vapor, and the vapor/liquid separation zone comprises a liquid withdrawal port, a liquid region, a vapor space and a vapor withdrawal port. In a further embodiment, the process can further comprise condensing the second stream from the product-catalyst separation zone prior to transferring the second stream to the syngas stripper.

In another embodiment, a process of the present invention comprises (a) contacting CO, $H_2$, and at least one $C_2$-$C_4$ olefin in a reaction zone in the presence of a hydroformylation catalyst to form at least one aldehyde product; (b) removing an aldehyde-containing liquid from the reaction zone and sending it to a product-catalyst separation zone, wherein the product-catalyst separation zone comprises a liquid withdrawal port and a vapor withdrawal port; (c) transporting a liquid comprising at least a portion of the hydroformylation catalyst, at least a portion of the aldehyde product, and unreacted olefin from the liquid withdrawal port to the reaction zone; (d) removing a vapor from the vapor withdrawal port, wherein the vapor comprises at least a portion of the aldehyde product, unreacted olefin, and one or more paraffins; (e) condensing the vapor to generate a second liquid; (f) transferring the second liquid to a syngas stripper wherein a gas comprising CO and $H_2$ separates the unreacted olefin from the aldehyde; (g) providing the gas leaving the syngas stripper to a condenser to provide a second liquid comprising a majority of the aldehyde, at least a portion of the unreacted olefin from the syngas stripper, and at least a portion of the paraffins from the syngas stripper, and to provide a gas stream comprising CO, $H_2$, the remainder of the unreacted olefin from the syngas stripper, and the remainder of the paraffins from the syngas stripper; (h) providing the gas stream leaving the condenser in (g) to the reaction zone; (i) transferring the second liquid from the condenser in (g) to a first distillation system wherein at least a portion of the unreacted olefin and paraffins are distilled from the aldehyde; (j) transferring the gas from the first distillation system to a second distillation system wherein the unreacted olefin and paraffins are separated into an olefin-enriched stream and a paraffin-enriched stream, wherein the gas is transferred from the first distillation system to the second distillation system without a compressor; and (k) transferring the olefin-enriched stream to the reaction zone.

In some embodiments, the rate of paraffin removal in step (j) is sufficient to prevent buildup of paraffin in the reaction zone.

The liquid from the condenser in step (g), in some embodiments, is transferred to the first distillation system with a pump.

In some embodiments, the aldehyde from the first distillation system is returned to the syngas stripper.

In some embodiments, transferring the olefin-enriched stream to the reaction zone comprises condensing the olefin-enriched stream and pumping the condensed olefin-enriched stream to the reaction zone.

The olefin-enriched stream in step (k), in some embodiments, is transferred to the reaction zone as a gas without a compressor.

Figure 1:
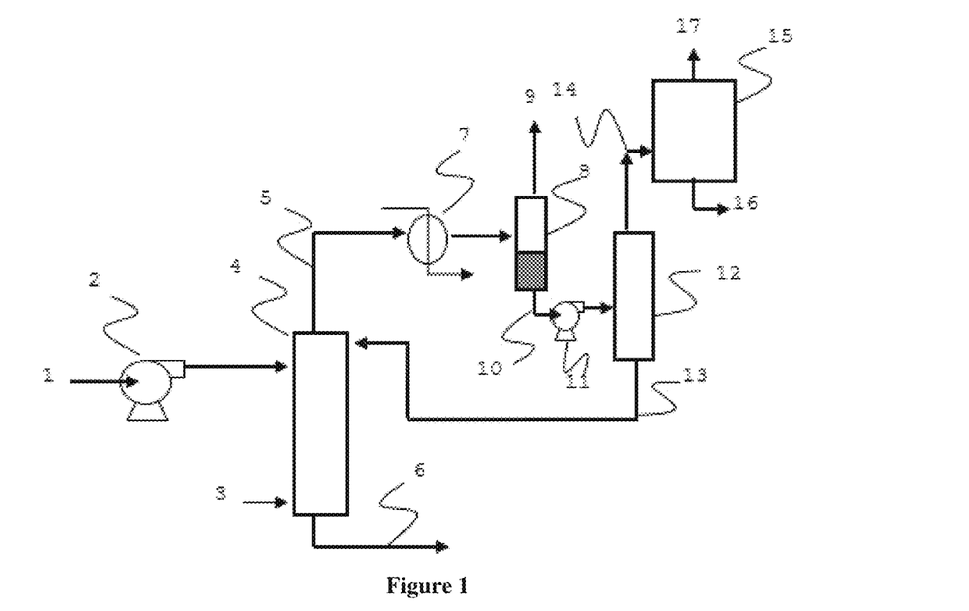
FIG. 1 is a schematic of one embodiment of the present invention showing the processing of crude product after hydroformylation product-catalyst separation.
Figure 2:
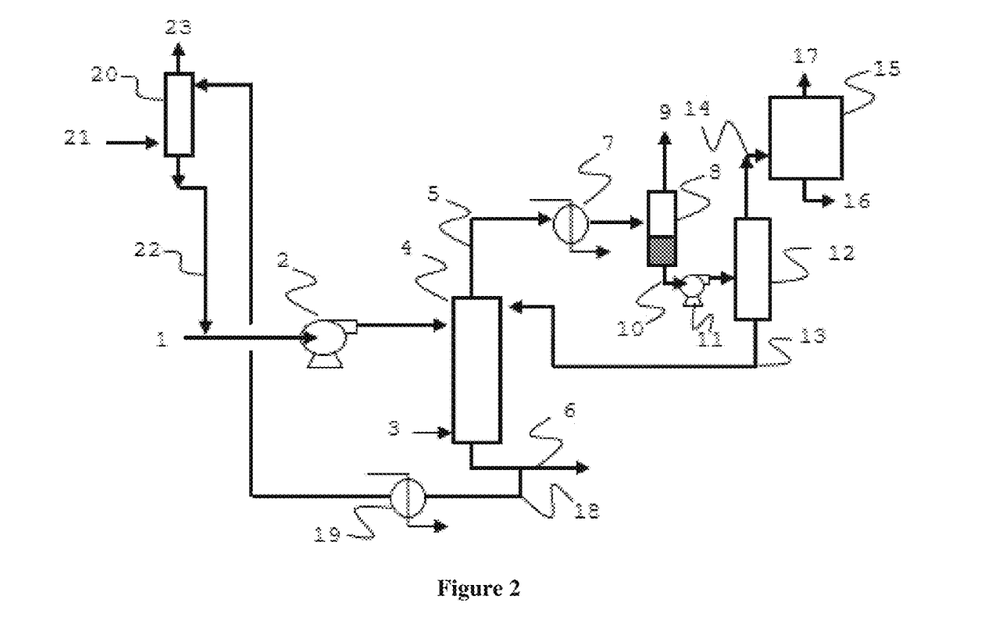
FIG. 2 is a schematic of another embodiment of the present invention showing the processing of crude product after hydroformylation product-catalyst separation with a vent scrubber.

Various embodiments of processes of the present invention are shown in FIGS. 1 and 2.

Referring to FIG. 1, initial crude aldehyde from a product-catalyst separation zone (e.g., vaporizer catch pot, not shown in FIG. 1), following a hydroformylation reaction zone, is introduced via stream (1) into pump (2) that delivers the predominantly liquid stream into a syngas stripper (4) at elevated pressure (an optional heater, not shown, may be used to adjust temperature). Syngas is introduced to the stripper via stream (3) and the resulting overhead gas stream containing the syngas, some aldehyde, and unreacted olefins is removed via line (5). Most of the aldehyde product leaves via line (6) for further processing but has essentially little, if any, unreacted olefin remaining. The overhead stream (5) is cooled by heat exchanger (7) and the resulting stream is sent to the gas/liquid separator (8) wherein the gas stream (9) is separated and sent to a hydroformylation reaction zone (not shown). The condensed phase in stream (10) is transferred using pump (11), optionally pre-heated with a heat exchanger (not shown), to distillation tower (12) wherein aldehyde is separated from the unreacted olefin and paraffins. The aldehyde is recycled back to the syngas stripper (4) via line (13). The substantially aldehyde-free olefin and paraffin stream (14) is then distilled in column (15) wherein the paraffins are removed via stream (16) and the olefin is removed via line (17).

An important advantage of embodiments of the present invention is that with olefins of four carbons or less, this recovery and recycle process does not require expensive compressors to deliver the olefin to reactor pressure or compressors to pressurize distillation columns to enable condensation of the olefins at conventional cooling water temperatures. In other words, there are no compressors required starting from pump (2) through the rest of the process. In addition, cryogenic cooling (e.g., cooling to temperatures below 20° C.) is also not required. By absorbing the volatile olefins into the aldehyde product and using liquid pumping to effect pressurization, compressors can advantageously be avoided. The distillations, especially the distillation used for the olefin/paraffin separation, can therefore be done at reactor pressures or pressures where the olefin is readily condensed with conventional cooling water and pumped as a liquid to reactor pressure. The use of the syngas stripper to effect the removal of olefin and paraffin from the bulk of the crude aldehyde at elevated pressure enables a very easy separation in the gas/liquid separator (8) without the need for a complex distillation tower wherein any carry over is recycled back to the system either via stream (9), (13), or (17). Stream (16) prevents the accumulation of paraffin in the hydroformylation reactor and can be sent for use as fuel or use in a syngas generator.

The syngas stripper (4) can be of a conventional design as taught, for example, in U.S. Pat. No. 5,087,763. The pressure in the stripper (4) is such that the syngas can continue on to a hydroformylation reaction zone as part of the total syngas employed in the hydroformylation reaction zone. The preferred pressure in the syngas stripper (4) is between 0.7 MPa (absolute) and 10 MPa, preferably between 0.8 MPa and 3.5 MPa, and most preferably between 1 MPa and 2.8 MPa. The operating temperature of the stripper is typically above 40° C., preferably above 80° C. but below 150° C. and most preferably below 110° C. Since evaporative cooling due to vaporization of the olefin and paraffin will occur in the syngas stripper (4), heating may be needed (not shown in FIG. 1). The exact pressure and temperature of the stripper will be determined by the pressure of the hydroformylation reaction system and the amount of olefin and paraffin to be removed (largely a function of raw material feed quality and catalyst efficiency) which are readily determined by those skilled in the art of distillation. ASPEN Plus Dynamics™ VLE modeling and similar protocols are well known in the art and can be used to determine such operating parameters.

Cooling of the overhead stream and gas/liquid separation in the separator (8) provides the syngas stream (9) that continues on to the hydroformylation reaction zone. Stream (9) is predominantly syngas, and also includes some unreacted olefin that can be recycled back to the reaction zone, but a large portion of the olefin and paraffin is dissolved in the condensed aldehyde at these pressures. Any entrained aldehyde in (9) will be recovered in the hydroformylation system. The amount of syngas flow through (4) need only be sufficient to strip most of the unreacted olefin from stream (1) and is not necessarily the entire syngas supply to the hydroformylation reaction system. In general, the mass flow of stream (3) is between 5 and 150% of the mass flow of stream (1) and preferably between 20 and 80%.

Distillation of the condensed phase in stream (10) to separate the aldehyde from the olefin and paraffin stream can advantageously be done at elevated pressure to avoid the need for cryogenic cooling of the olefin and paraffin overhead stream (14). Such pressures do necessitate elevated temperatures, however, which normally would be avoided since elevated temperature conditions can generate aldehyde condensation heavies. Surprisingly, the observed heavies formation rate is quite low, presumably because the material has already been distilled at least once such that most of the known heavies promoters (e.g., metal salts, acids, bases, other heavies (e.g., dimers) and the like) have been removed. The concentration of aldehyde in stream (10) is at least 25% lower than stream (1) as well due to the prior distillation. Additionally, the distillation in (12) need not be quantitative in that any olefin in stream (13) will be recycled. This means that the temperature in the column can be substantially less than those in the prior art (~130° C. as compared to 190° C. in U.S. Pat. No. 4,287,369, for example). The distillation column (12) conditions are preferably such that the amount of aldehyde leaving the top of the column via stream (14) is minimized since this material is lost in stream (16). The pressure in column (12) is determined by the pressure in column (15) which itself is a function of the conditions needed to separate the olefin and paraffin. Thus, it is desirable to determine the conditions in column (15) first, and then set the conditions in column (12) (e.g, pressure and temperature) to effect the aldehyde separation and have stream (14) flow into column (15) without needing a compressor.

Column (15) is operated at elevated pressure to avoid cryogenic cooling of the overhead olefin stream (17). In most cases, this stream pressure can be greater than the hydroformylation reactor pressure such that stream (17) can be sent directly to the reaction system as a gas (e.g., combined with the syngas from the stripper (4)). This conveniently allows any syngas that entered column (12) from stream (10) to be returned to the reaction zone. Alternatively, stream (17) can be condensed to a liquid with a condenser (not shown in FIG. 1) and pumped to the reaction zone. Of course, depending on the hydroformylation reaction pressure and the olefin, the conditions in column (15) will vary. For example, for a propylene-based hydroformylation process, the pressure in (15) should be above 1 MPa, preferably above 1.5 MPa, and most preferably above 2 MPa but below 7 MPa and preferably below 3.5 MPa. The distillation of propylene and propane (or other hydrocarbons) is well known and conditions for this separation can readily be determined once the delivery pressure of stream (17) has been established. The latter is usually determined by either the pressure of the hydroformylation reaction system (if stream (17) is being delivered as a gas) or the condenser conditions (e.g., the cooling water temperature) on stream (17) if the olefin is being recycled as a liquid.

The olefin/paraffin separation column (15) can be operated to determine the purity of either stream (16) or (17). Since there is little to no aldehyde present, the temperature and exposure time are not critical. In general, stream (17) contains substantial amounts of paraffin. A key consideration is that the paraffin leaving in stream (16) should be sufficient to remove the paraffin present in the incoming feeds (e.g., stream (1)) as well as any paraffin generated by hydrogenation side reactions to prevent paraffin from building up in the system. The amount of olefin in stream (16) is typically kept at a minimum since it is lost. Other inerts such as $N_2$, Ar, and $CH_4$ may also need to be vented, typically via the reactor vents but an optional purge on line (17) (not shown) may be employed.

It will be understood that the first two separation vessels (syngas stripper (4) and first distillation column (12)) are configured such that a stream recovered from at or near the bottom of the second separation vessel (12) is passed to the first separation vessel (4) and a stream recovered from at or near the top of the first separation vessel (4) is passed to the second separation vessel (12). Thus a recycle loop is established between the first and second separation vessels. Since the syngas stripper (4) operates at lower temperatures than a conventional distillation tower, the temperature exposure for the aldehyde-rich stream is reduced as compared to prior art designs.

It will be understood that the two separation vessels (syngas stripper (4) and first distillation column (12)) operate such that the heavier component in the feed stream to the first separation vessel (4), is removed from at or near the bottom of the first, lower pressure, separation vessel (4). In this case, the heavier component is the product aldehyde being removed via stream (6). It will be further understood that the above two separation vessels operate such that at least some of the heavier component in at least one feed stream to the first separation vessel (4), is obtained from at or near the bottom of the second, higher pressure, separation vessel (12) which is represented as stream (13) in FIG. 1. The overhead stream from the first separation vessel (4) will comprise a mixture of heavy and light components. These are sent to the second separation vessel which is typically operated at a higher pressure than the first (wherein the pressure increase supplied by a liquid pump (11) rather than a compressor). In this second separation vessel (12), the lighter component in the feed stream is removed as overhead from the second column and a mixture of heavy and light components is removed from the bottom and returned to the first, typically lower pressure separation vessel via line (13) while the aldehyde-free hydrocarbon stream (14) is sent for further processing. Thus each separation vessel provides one stream of a purified component and a stream which comprises a mixture of components such that the reduced temperature difference between top and bottom can be used. In this connection, it should be understood that complete separation in a single vessel would require a larger temperature difference.

Having the first and second vessels operating at different pressures allows the temperature of the bottom of the first separation vessel operating at a lower pressure to remain relatively low so that the production of heavy by-products is reduced and preferably avoided. The use of a gas-stripping column (rather than a conventional distillation column) as the first vessel allows for a substantially reduced distillation temperature. Further the inclusion of a second separation vessel operated at a pressure that is higher than that in the first separation vessel allows an appropriate temperature to be used such that the stream recovered from at or near the top of the second separation vessel can be condensed using cooling water rather than expensive refrigeration equipment.

Thus the present invention enables a lower temperature difference between the first component stream (e.g., stream (6)) and the second component stream (e.g., stream (14)) to be used than is achievable where a single separation vessel, such as a distillation column, is used. In this regard, it should be understood that a conventional single separation column using cooling water would result in a higher temperature for the stream recovered from the bottom for the same level of separation.

Another embodiment of the invention is shown on FIG. 2 wherein a vent scrubber is included. A vent scrubber similar to that shown In U.S. Pat. No. 4,210,426 can be used, for example, in such embodiments. A portion of stream (6) is diverted through an optional heat exchanger and cooled prior to entering an absorption tower (20). Hydroformylation reaction zone vents (21) are sent through the bottom of the tower in a counter-current fashion against the aldehyde absorbing fluid which exits the tower via line (22) and is combined with stream (1) or alternatively into streams (10) or (13) with a pump. Unabsorbed gases exit the tower via line (23) and are sent to flare or the fuel header. Stream (23) typically is composed of uncondensible lights such as CO, $H_2$, $N_2$, Ar, and $CH_4$. Tower (20) is preferably cooled to avoid elevated temperatures to compensate for heat brought in with stream (21) or from positive heat of absorption of components; this can be accomplished by cooling jackets, cooling coils, or cooling zones between sections within the tower (intercoolers). The absorber tower (20) or stream (23) is optionally cooled prior to exiting the tower to maximize olefin absorption and minimize aldehyde losses, preferably below 80° C. and most preferably below 50° C. The absorber tower preferably operates at or slightly below the hydroformylation reactor pressures (typically above 0.5 MPa and preferably above 0.6 MPa) to avoid the need for compressors such that the amount of aldehyde loss in (23) at these temperatures and pressures is very low. Of course, multiple absorption towers can be used to treat different vents at different pressures since pumps (not shown) can be used to deliver the aldehyde absorbing fluid at any desired pressure. In general though, pump (2) should deliver sufficient pressure to service any vent scrubber tower.

The source of the vents represented by stream (21) can include reactor vents, knockout pot vents, pressure control vents, high and low pressure vaporizer vents, and aldehyde refining vents. Since the primary location of olefin loss in the vent streams is typically the reactor vents (used to purge inerts), the reactor vents are the preferred source of stream (21). Stream (18) can be added at a single point or a plurality of points within the tower (20) and a liquid recycle from (22) into (18) (not shown) may be used to maintain a consistent flow of liquid in the tower.

EXAMPLES

All parts and percentages in the following examples are by weight unless otherwise indicated. Pressures are given as absolute pressure unless otherwise indicated.

Example 1

A conventional Oxo reaction system with two identical CSTR reactors similar to that depicted in FIG. 4.6 of Process Economics Program Report 21D, OXO ALCOHOLS (December 1999), available from IHS Inc., is modeled using chemical process simulation software. No compressors were employed in the simulation. The catalyst is a typical Rh-TPP catalyst as described in U.S. Pat. No. 4,148,830 (ex. 13), and the reaction conditions are essentially those of Example 13 of that patent for propylene except that the initial target rhodium concentration for the first reactor is 250-350 ppm Rh. The TPP concentration is approximately 10-11% in the reactors. Selected process conditions and the rate of unrefined aldehyde production are shown in Table 1 based on a olefin feed rate of 33700 kg/hr of propylene (90-95% purity).

Selected process conditions and the rate of unrefined aldehyde production are shown in Table 1 based on FIG. 1 (stream numbers in Table 1 correspond with those in FIG. 1).

TABLE 1

| Mole % compositions of streams based on FIG. 1 (flows in kg/h unless otherwise indicated). | | | | | | | |
|---|---|---|---|---|---|---|---|
| | Stream 1 | Stream 6 | Stream 9 | Stream 10 | Stream 13 | Stream 14 | Stream 16 | Stream 17 |
| $H_2$—CO | ND | 0-0.3 | 31.4-31.3 | ND | ND | 1.2-2.1 | ND | 3-5.5 |
| Propylene | 0.8 | ND | 9.4 | 7.4 | 4.6 | 25 | 1.9 | 61.3 |
| Propane | 2.2 | ND | 25.8 | 20 | 13 | 69.3 | 98.1 | 21.6 |
| Aldehyde | 96.8 | 99.5 | 1.2 | 72 | 82.2 | 0.01 | 0.03 | ND |
| T (° C.) | 135 | 96 | ~40 | 121 | 123 | 61 | 68 | 60 |
| Pressure (kPa) | 2199 | 2199 | 2013 | 2496* | 2496 | 2496 | 2378 | 2378 |
| Flow | Varies | 49896 | 277 standard $m^3$/min | 5625 | 60782 | 4128 | 2699 | 1474 |

ND = Not determined (typically below detection limit).
*After pump (11).

Stream (1) is heated to 135° C. just prior to entering stripper (4) and the exit temperature of stream (6) is 98° C. The stream (9) flow varies as the production rate varies (thus Stream (1) flow varies) but stream (9) mass flow is approximately 25% higher than the stream (1) mass flow. Stream (9) volume flow is typically about 40-160% larger than that of stream (3) depending on the amount of olefin and paraffin in stream (1). The amount of propane leaving the system in stream (16) is sufficient to maintain the amount of propane in the system at low levels yet allows full recycle of the propylene feed.

Example 2

An absorption tower (20), in the form of a vent scrubber, as depicted in FIG. 2 is used to scrub the reactor #2 purge vent (the equivalent of stream (7) in FIG. 4.6 of Process Economics Program Report 21D, OXO ALCOHOLS (December 1999)). Unless otherwise stated, references to equipment or streams in this Example 2 correspond to FIG. 2. The stream from the purge vent (21) is added to the middle of the absorption tower (20). The absorption tower (20) for this simulation included 33 trays. The output from the high pressure vaporizer (the equivalent of stream (11) in FIG. 4.6 of Process Economics Program Report 21D, OXO ALCOHOLS (December 1999)) is added at the bottom of the absorption tower (20) and the combined gas flow is contacted with stripped aldehyde and the bottom stream is combined with stream (10). The results shown in Table 2 show a very high recovery of olefin from the vents with very minimal aldehyde losses. The remainder of the composition in streams (21) and (23) are $N_2$ and $CH_4$ thus providing a suitable purge of these inerts from the system.

TABLE 2

Mole % compositions of absorption tower streams based on FIG. 2 (flows in kg/h unless otherwise indicated).

|  | Stream 21 | Stream 23 |
|---|---|---|
| $H_2$—CO | 9-4.3 | 17-12 |
| Propylene | 14 | 2.2 |
| Propane | 38.7 | 10 |
| Aldehyde | 1 | 3 |
| T (° C.) | ~40 | 32 |
| Pressure (kPa) | 2013 | 655 |
| Flow | 1742 | 943 |

Various embodiments of the present invention offer a number of advantages: (1) recovery and recycle of unreacted olefin, (2) avoidance of compressors and cryogenic cooling (lower capital expense) with lower molecular weight olefin feeds, (3) enablement of use of lower grade olefins (higher alkane concentration) without excessive vent losses, (4) avoidance of excessive heavies formation in distillation of olefin/aldehyde mixtures, and/or (5) the syngas used in the stripping process is used in the hydroformylation reaction thus is not wasted.

What is claimed is:

1. A process comprising:
  (a) contacting CO, $H_2$, and at least one $C_2$-$C_4$ olefin in a reaction zone in the presence of a hydroformylation catalyst to form at least one aldehyde product;
  (b) removing an aldehyde-containing liquid from the reaction zone and sending it to a product-catalyst separation zone;
  (c) transporting a first stream from the product-catalyst separation zone to the reaction zone, wherein the first stream is a liquid comprising at least a portion of the hydroformylation catalyst, at least a portion of the aldehyde product, and unreacted olefin;
  (d) removing a second stream from the product-catalyst separation zone, wherein the second stream comprises at least a portion of the aldehyde product, unreacted olefin, and one or more paraffins;
  (f) transferring the second stream to a syngas stripper wherein a gas comprising CO and $H_2$ separates the unreacted olefin from the aldehyde;
  (g) providing the gas leaving the syngas stripper to a condenser to provide a second liquid comprising a majority of the aldehyde, at least a portion of the unreacted olefin from the syngas stripper, and at least a portion of the paraffins from the syngas stripper, and to provide a gas stream comprising CO, $H_2$, the remainder of the unreacted olefin from the syngas stripper, and the remainder of the paraffins from the syngas stripper;
  (h) providing the gas stream leaving the condenser in (g) to the reaction zone;
  (i) transferring the second liquid from the condenser in (g) to a first distillation system wherein at least a portion of the unreacted olefin and paraffins are distilled from the aldehyde;
  (j) transferring the gas from the first distillation system to a second distillation system wherein the unreacted olefin and paraffins are separated into an olefin-enriched stream and a paraffin-enriched stream, wherein the gas is transferred from the first distillation system to the second distillation system without a compressor; and
  (k) transferring the olefin-enriched stream to the reaction zone.

2. The process of claim 1, wherein the second stream from the product-catalyst separation zone is a liquid.

3. The process of claim 2, wherein the product-catalyst separation zone comprises a membrane separation process.

4. The process of claim 1, wherein the second stream from the product-catalyst separation zone is a vapor.

5. The process of claim 4, wherein the product-catalyst separation zone comprises a vaporizer.

6. The process of claim 4, wherein the product-catalyst separation zone comprises a vaporizing zone and a vapor/liquid separation zone, wherein the aldehyde-containing liquid from the reaction zone is heated in the vaporizing zone to generate the vapor, and wherein the vapor/liquid separation zone comprises a liquid withdrawal port, a liquid region, a vapor space and a vapor withdrawal port.

7. The process of claim 4, further comprising condensing the second stream from the product-catalyst separation zone prior to transferring the second stream to the syngas stripper.

8. The process of claim 1, wherein the rate of paraffin removal in step (j) is sufficient to prevent buildup of paraffin in the reaction zone.

9. The process of claim 1, wherein the liquid from the condenser in (g) is transferred to the first distillation system with a pump.

10. The process of claim 1, wherein the aldehyde from the first distillation system is returned to the syngas stripper.

11. A process comprising:
  (a) contacting CO, $H_2$, and at least one $C_2$-$C_4$ olefin in a reaction zone in the presence of a hydroformylation catalyst to form at least one aldehyde product;
  (b) removing an aldehyde-containing liquid from the reaction zone and sending it to a product-catalyst separation zone, wherein the product-catalyst separation zone comprises a liquid withdrawal port and a vapor withdrawal port;
  (c) Transporting a liquid comprising at least a portion of the hydroformylation catalyst, at least a portion of the aldehyde product, and unreacted olefin from the liquid withdrawal port to the reaction zone;
  (d) removing a vapor from the vapor withdrawal port, wherein the vapor comprises at least a portion of the aldehyde product, unreacted olefin, and one or more paraffins;
  (e) condensing the vapor to generate a second liquid;
  (f) transferring the second liquid to a syngas stripper wherein a gas comprising CO and $H_2$ separates the unreacted olefin from the aldehyde;
  (g) providing the gas leaving the syngas stripper to a condenser to provide a second liquid comprising a majority of the aldehyde, at least a portion of the unreacted olefin from the syngas stripper, and at least a portion of the paraffins from the syngas stripper, and to provide a gas stream comprising CO, $H_2$, the remainder of the unreacted olefin from the syngas stripper, and the remainder of the paraffins from the syngas stripper;

(h) providing the gas stream leaving the condenser in (g) to the reaction zone;

(i) transferring the second liquid from the condenser in (g) to a first distillation system wherein at least a portion of the unreacted olefin and paraffins are distilled from the aldehyde;

(j) transferring the gas from the first distillation system to a second distillation system wherein the unreacted olefin and paraffins are separated into an olefin-enriched stream and a paraffin-enriched stream, wherein the gas is transferred from the first distillation system to the second distillation system without a compressor; and (k) transferring the olefin-enriched stream to the reaction zone.

12. The process of claim 11, wherein the rate of paraffin removal in step (j) is sufficient to prevent buildup of paraffin in the reaction zone.

13. The process of claim 11, wherein the second liquid from the condenser in (g) is transferred to the first distillation system with a pump.

14. The process of claim 1, wherein the aldehyde from the first distillation system is returned to the syngas stripper.

15. The process of claim 1, wherein transferring the olefin-enriched stream to the reaction zone comprises condensing the olefin-enriched stream and pumping the condensed olefin-enriched stream to the reaction zone.

16. The process of claim 1, wherein the olefin-enriched stream in step (k) is transferred to the reaction zone as a gas without a compressor.

* * * * *